United States Patent [19]

Smith et al.

[11] 4,260,467

[45] Apr. 7, 1981

[54] STATIC DROP MERCURY ELECTRODE

[75] Inventors: John L. Smith, Mercerville; Bruce N. Whitlock, Pennington, both of N.J.

[73] Assignee: Princeton Applied Research Corporation, Princeton, N.J.

[21] Appl. No.: 872,506

[22] Filed: Jan. 26, 1978

[51] Int. Cl.³ ............................................. G01N 27/34
[52] U.S. Cl. ................................................. 204/195 H
[58] Field of Search ........................ 204/195 H; 324/31

[56] References Cited

U.S. PATENT DOCUMENTS

| | | | |
|---|---|---|---|
| 2,281,051 | 4/1942 | Roger | 222/340 |
| 2,361,295 | 10/1944 | Kanner et al. | 324/31 |
| 2,728,721 | 12/1955 | Ladisch et al. | 204/195 H |
| 2,745,803 | 5/1956 | Leveque | 204/195 H |
| 2,849,391 | 8/1958 | Ladisch | 204/195 H |
| 2,921,715 | 1/1960 | Asset et al. | 222/70 |
| 3,281,348 | 10/1966 | Schumacher et al. | 204/195 H |
| 3,367,858 | 2/1968 | Kurosaki | 204/195 H |
| 3,421,989 | 1/1969 | Haagen-Smit | 204/195 H |
| 3,808,116 | 4/1974 | Webb | 204/195 H |

FOREIGN PATENT DOCUMENTS

| | | |
|---|---|---|
| 674139 | 6/1952 | United Kingdom . |
| 936724 | 9/1963 | United Kingdom . |
| 936725 | 9/1963 | United Kingdom . |
| 1089600 | 11/1967 | United Kingdom . |
| 515061 | 9/1976 | U.S.S.R. ................ 204/195 H |

OTHER PUBLICATIONS

Valeriote et al., "Chemical Instrumentation", 1(2), pp. 153–167, Oct. 1968.
Peterson, "Am. Lab.", No. 12, pp. 69–78, Dec. 1979.
Bond, "Modern Polarographic Methods in Analytical Chemistry", pp. 165–166, 1980.
Heineman et al., "Analytical Chemistry 1980 Fundamental Reviews", pp. 136 R–151 R, 1980.
Brinkmann, "Hanging Mercury Drop Electrode", Product Bulletin, No. 175, 2/74.
Yamazaki, "Balanced Head Stationary Hanging Mercury Drop Electrode in Anodic Stripping Polarography", Review of Polarography (Japan), vol. 13, No. 1, 1964, pp. 26–28.
Yamazaki, "Study on Anodic Stripping Polarography with the Balanced Head Stationary Hanging Mercury Drop Electrode", Review of Polarography (Japan), vol. 17, Nos. 5–6, 1971, pp. 121–132.

*Primary Examiner*—T. Tung
*Attorney, Agent, or Firm*—Finnegan, Henderson, Farabow, Garrett & Dunner

[57] ABSTRACT

Mercury flow from a reservoir of mercury to a mercury drop capillary extending vertically downward from the reservoir is governed by selective engagement of a sealing surface immersed in the mercury reservoir with a valve seat also immersed in the mercury reservoir to allow for controlled formation of mercury drops at the lower end of the capillary which drops, after formation, are held non-growing or static. The capillary is removable from the housing and when so removed the sealing surface engages the housing of the reservoir to prevent loss of mercury from the reservoir.

20 Claims, 5 Drawing Figures

STATIC DROP MERCURY ELECTRODE

BACKGROUND

The present invention relates to a static drop mercury electrode and more particularly to a valve control for the formation of the static drops.

Polarography, one of a broad class of voltametric techniques, provides chemical analysis of substances in electrolyte solution by the observation of current and voltage relationships at electrodes immersed in the solution. At low voltages no current flows between the electrodes. However, as the voltage is increased and becomes great enough for deposition of each reducible substance in solution on the electrodes, current begins to flow. Generally, the magnitude of the current is proportional to the concentration of the reducible substance in solution and the magnitude of the voltage potential required to induce this current flow is indicative of the density of the substance in solution. Thus, precise measurement of the current through the immersed electrodes, as a function of applied potential, provides both qualitative and quantitative analysis of the reducible substances in solution.

The electrical and chemical antithesis of polarography is the technique of stripping voltametry whereby the reducible substances in solution are concentrated by plating the substances onto an immersed electrode. Plating is accomplished by holding an immersed electrode at suitable potential. The applied potential is then varied in the anodic direction, with the plated electrode biased toward increasingly more positive values. The substances plated on the electrode oxidize into solution at potentials corresponding to the oxidation potentials of the plated substances. Again, current flow occurs with the oxidation of each substance and analysis of the substances is achieved in a manner analogous to the polarographic analysis described above.

Typical polarographic and stripping voltametry apparatus consists of a variable voltage source, a current measuring circuit and an electrolysis cell. The cell typically contains three electrodes immersed in the solution. The three electrodes comprise a reference electrode at which the variable potential is applied, a working or indicator electrode at which current flow is measured, and an auxiliary or counter electrode which regulates the potential between the reference and working electrodes.

The most widely used working or indicator electrode is the dropping mercury electrode, which consists of a fine bore capillary tube above which a constant head of mercury is maintained. The mercury emerges from the tip of the capillary at the rate of a few milligrams per second and forms spherical droplets which fall from the capillary orifice into the solution at a typical rate of one every two to ten seconds. The capillary comprising such a dropping mercury electrode must have a small enough bore so that the adhesion between a mercury drop and a column of mercury above the drop, the cohesion of the mercury column and the interfacial tension between the drop and the solution under test is sufficient to allow the drop to form. When the bore of the capillary exceeds approximately twelve hundredths of an inch, the drop no longer is able to hang at the orifice of the capillary. A suitable capillary comprises, for example, marine barometer tubing of three thousandths of an inch bore. Capillary of a fine bore type capable of establishing mercury drops is hereafter referred to as a "dropping mercury capillary."

The dropping mercury electrode has a number of advantages over other varieties of electrodes. First, mercury has a hydrogen over-voltage which allows observation of processes which would normally be obscured by the decomposition of water at other electrodes. In addition, periodic renewal of the surface area of the dropping mercury electrode minimizes problems due to surface composition changes.

However, since the inception of polarography, all voltametric measurements at a dropping mercury electrode have been complicated by the time dependence of the surface area of the growing mercury drop. More specifically, a double-layer charging current is produced by the growth of the mercury drop which varies as the drops grow and, hence, interferes with obtaining accurate polarographic measurements.

Prior art techniques have attempted to overcome the disadvantages of a dropping mercury electrode by the use of pulse polarographic techniques in connection with a drop kicker in an attempt to minimize the effects of drop growth during voltametric analysis by assuring analysis occurs during the same period of growth for each drop. Basically, the drop kicker of the prior art applies a periodic mechanical pulse to the capillary, disengaging the mercury drop hanging therefrom. The dislodgement of the drop serves as a starting point for the timing of a subsequently developed drop. A potential pulse is applied to the mercury drop a fixed time after activation of the drop kicker in an attempt to assure that the polarographic measurement is taken with a drop of given repeatable size. While the pulse polarographic technique employing a drop kicker represents an improvement over the standard dropping mercury electrode, nevertheless, during sampling, the mercury drop is increasing in size causing imprecise resultant measurements.

Another prior art technique establishes a stationary hanging mercury drop at the end of a capillary tube by selectively decreasing the height of the mercury column after formation of a drop to prevent additional drop growth. In this technique a single hanging drop is held stationary at the end of the capillary for a long time, on the order of thirty minutes. While this technique results in a constant area mercury drop, a single drop is required to be held stationary for so long that the surface of the drop is subject to composition change which interfers with the accuracy of the measurements obtained. Furthermore, high analysis resolution by rapid removal and replacement of drops and repetitive measurements cannot be achieved by this prior art technique.

Still another form of prior art mercury electrode employs a relatively large bore capillary formed with a U-shape adjacent its lower end which allows the end of the capillary to support the resultant sessile drop. In this form of apparatus, it has been suggested to employ a form of sliding gate valve in the large bore capillary which may periodically be opened and closed to form constant area sessile drops supported on the end of the large bore U-shaped tubing. Such a system has little commercial or scientific value since the sessile drop of that system does not and cannot have the desired spherical geometry of a hanging mercury drop, is susceptible to causing solution contamination of the large bore capillary and is more difficult to dislodge than a hanging drop. Furthermore, hanging mercury drops cannot be formed by the employment of sliding gate valves since a hanging mercury drop requires employment of a dropping mercury capillary of fine bore and sliding gate valves for such fine bore capillaries inherently trap small volumes of air. Moreover, sliding gate valves of the prior art, even in large capillary systems, cannot adequately isolate the mercury column from air which, if introduced into the column in even the smallest of amounts, a fraction of a microliter, seriously interferes with the stability of a hanging mercury drop.

It must be understood, to appreciate the significance of even the smallest amount of air in a mercury column, that it acts as a spring in the system so that after a drop which has been hanging on the capillary tip falls, the pocket formed by the air contracts and the resultant pressure differential pulls the solution part way up the capillary, thereby contaminating the capillary. Furthermore, even the smallest amount of air may sporadically break loose and flow down the capillary causing breaks in the required electrical continuity of the capillary.

The problem of trapped air particularly affects an additional prior art mercury drop electrode employing a plunger delivery system for dispensing mercury drops. A typical prior art plunger delivery system consists of a dropping mercury capillary with an enlarged bore at its upper end. A plunger is fitted at this bore to form a seal with the bore. The bore is filled with mercury and the plunger is advanced down the bore and drops of mercury form at the capillary tip. As is true with sliding gate valves, the seal between the bore and the plunger inevitably introduces air into the mercury system since the high surface tension of mercury readily traps bubbles of air against the capillary bore and around the plunger seal. Another shortcoming of the plunger delivery system is that minute variations in the bore diameter or bore-to-plunger friction can materially affect the drop size as the plunger advances down the bore. Furthermore, such a system is costly in that it requires several precision parts including a motorized micrometer screw drive for advancing the plunger.

It should also be noted that in none of the above-mentioned prior art techniques can the dropping mercury capillary be readily removed from the electrode or inserted into the electrode without spillage of mercury.

It is accordingly an object of the present invention to provide a static mercury drop electrode for periodically generating static mercury drops of reproducible size at the end of a dropping mercury capillary.

It is another object of the present invention to provide a static mercury drop electrode for generating static mercury drops of predetermined size in which air is prevented from interfering with the operation of the capillary.

It is still another object of the present invention to provide a static memory drop electrode in which predetermined amounts of mercury are allowed to flow down a dropping mercury capillary, without the introduction of air into the capillary, to allow for the formation of static mercury drops of reproducible size at the lower end of the dropping mercury capillary.

Another object of the present invention is to provide a static mercury drop electrode in which a dropping mercury capillary is readily replaceable without the introduction of air into the mercury system.

A still further object of the present invention is to provide a mercury drop electrode which can readily be employed as a dropping mercury electrode, hanging mercury drop electrode and as a static drop mercury electrode without physical changeover.

Additional objects and advantages of the present invention will be set forth in part in the description which follows and in part will be obvious from the description or may be learned by practice of the invention. The objects and advantages may be realized and obtained by means of the instrumentalities and combinations particularly pointed out in the appended claims.

SUMMARY OF THE INVENTION

To achieve the foregoing objects and in accordance with the purposes of the invention, as embodied and broadly described herein, the static mercury drop electrode of the present invention comprises a housing forming a reservoir for liquid mercury or other similar fluid; a dropping mercury capillary having first and second ends and forming a capillary passage therebetween with said capillary passage terminating in a downward direction at said second end and a valve for selective air-purging passage of mercury from the reservoir to the first end of the capillary to form static mercury drops at the second end of the capillary. The valve, in a preferred embodiment, includes a first valve seat position in the reservoir beneath the surface of the mercury. The valve further includes a sealing mechanism for forming a sealing surface, and a control mechanism for selectively controlling the relative position of the sealing surface and the first valve seat between an open position with the sealing surface disengaged from the first valve seat to allow passage of the mercury from the reservoir to the capillary, and a closed position with sealing surface engaged with the first valve seat to prevent passage of the mercury from the reservoir to the capillary.

In a preferred embodiment of the present invention, the first end of the capillary actually forms the first valve seat and the first end of the capillary is located above the lowermost portion of the reservoir, causing the first end of the capillary to be surrounded by mercury in the open position of the valve.

In a further preferred embodiment of the present invention, the sealing mechanism comprises a plunger with the sealing surface formed on one end thereof, the plunger being mounted in the housing for slidable movement by the control mechanism to selectively engage and disengage the first valve seat.

The control mechanism, in accordance with one embodiment of the present invention, includes a spring biasing the sealing surface of the plunger into one of the positions and further includes a solenoid selectively operable on the plunger to bias the sealing surface into the other position.

In a still further embodiment of the present invention, the housing has a second valve seat adjacent a capillary opening in the housing through which the first end of the capillary removeably extends to form the first valve seat and furthermore, the sealing surface of the plunger is biased by the control mechanism in a manner whereby, upon removal of the capillary from the housing, the sealing surface engages the second valve seat to prevent escape of mercury from the reservoir through the capillary opening upon removal of the capillary.

DESCRIPTION OF THE DRAWINGS

A greater appreciation of the objects and advantages of the invention may be understood by a detailed description taken in conjunction with the drawings, wherein.

DETAILED DESCRIPTION

Reference will now be made in detail to the present preferred embodiment of the invention, an example of which is illustrated in the accompanying drawings.

Figure 1:
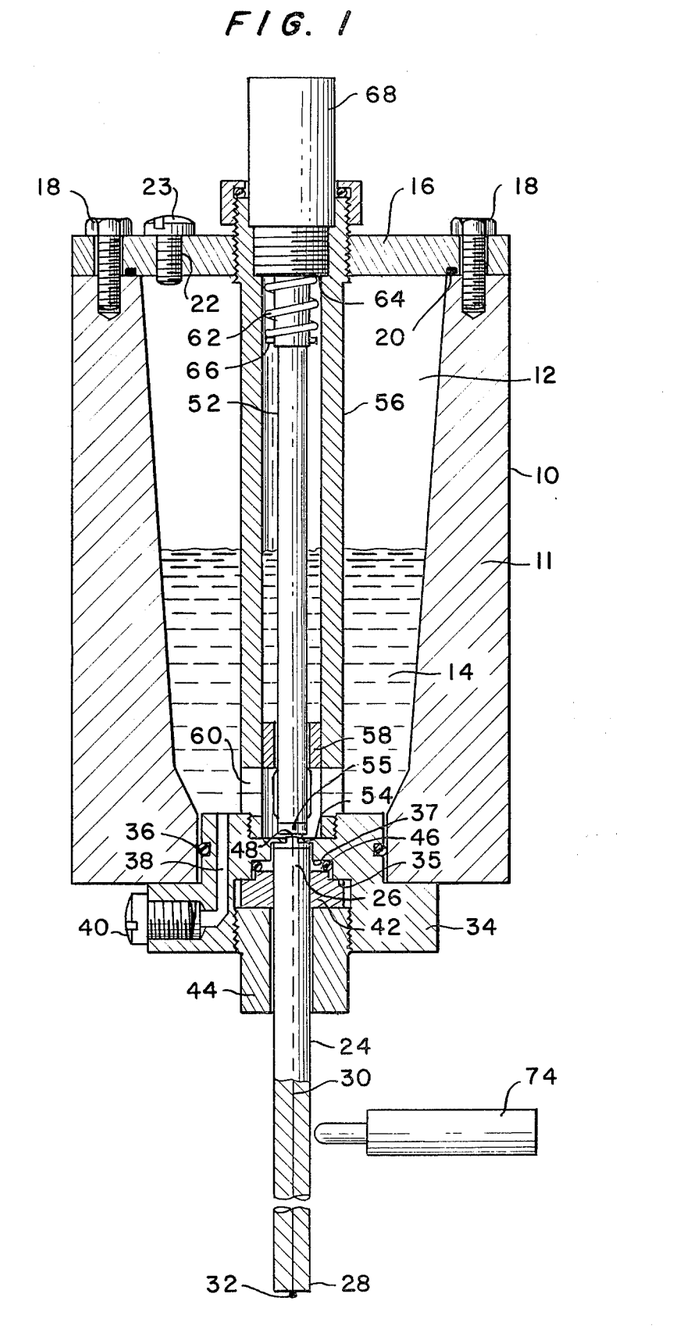
FIG. 1 is a sectional diagram of a preferred embodiment of a static drop mercury electrode in accordance with the teachings of the present invention.

Referring to FIG. 1, there is shown a preferred embodiment of a static drop mercury electrode incorporating the teachings of the present invention.

In accordance with the present invention, the static drop mercury electrode illustrated in FIG. 1 comprises a housing 10 forming a reservoir 12 for liquid mercury 14. The housing 10 is preferably formed of stainless steel or other material having no chemical reaction with mercury. Furthermore, it should be understood throughout the specification that other fluids such as gallium, which is fluid at a slightly elevated temperature, can be substituted for mercury and employed in accordance with the teachings of the present invention. Thus, hereinafter, the use of the term mercury is intended to refer to mercury and to all other materials substitutable therefor.

Returning to FIG. 1, housing 10 is shown to include generally cylindrical shaped sidewalls 11. A cover 16 is held fast against the upper end of the sidewalls 11 of housing 10, by screws or other suitable fastening devices 18. O-ring 20 assures that the seal between cover 16 and sidewalls 11 is air-tight. Furthermore, opening 22, removeably filled by screw 23, allows for access to reservoir 12 through cover 16. The lower end of sidewalls 11 is closed by a bottom plug 34. A sealed engagement between bottom plug 34 and sidewalls 11 of housing 10 is assured by O-ring 36 held fast in a channel surrounding the outside of bottom plug 34 and in sealed engagement with sidewalls 11. Bottom plug 34 contains a large bore passage 38 which selectively provides access to reservoir 12 and can receive a source of nitrogen or other pressurizing inert gas. Passage 38 can also be closed off by a screw 40 mounted in passage 38.

The static drop mercury electrode illustrated in FIG. 1 includes a dropping mercury capillary 24 having a first end 26 and a second end 28. Capillary 24 has a capillary passage 30 formed therein between first end 26 and second end 28 with capillary passage 30 terminating in a downward direction at second end 28. Capillary passage 30 is formed by a small diameter bore through capillary 24 not exceeding twelve hundredths of an inch in diameter. In a preferred embodiment of the present invention, dropping mercury capillary 24 extends vertically downward from housing 10 and more specifically from bottom plug 34.

Bottom plug 34 has an opening from the bottom portion thereof to removeably receive dropping mercury capillary 24. More specifically, capillary 24 is surrounded by a ferrule 42 formed, for example, of metal or plastic and held fast to capillary 24 a selected distance below first end 26 by gluing or other suitable means. Ferrule 42 is positioned at a selected distance below the termination of first end 26 so that when capillary 24 is inserted into the opening of bottom plug 34 ferrule 42 engages inwardly extending shoulders 35 of bottom plug 34 to hold capillary 24 in fixed vertical extension from the bottom of reservoir 12. Ferrule 42 may, for example, be held fast to housing 10 by a suitable capillary nut 44 threadably inserted into the lower opening of bottom plug 34. Furthermore, an O-ring 46 may be employed between ferrule 42 and the inwardly extending shoulders 37 of bottom plug 34 to establish a seal between dropping mercury capillary 24 and housing 10.

In accordance with the teachings of the present invention, the static mercury drop electrode illusrated in FIG. 1 includes valve means for providing selective air-purging passage of mercury from a mercury reservoir to a first end of a dropping mercury capillary to form static mercury drops at the second end of the capillary.

Figure 2:
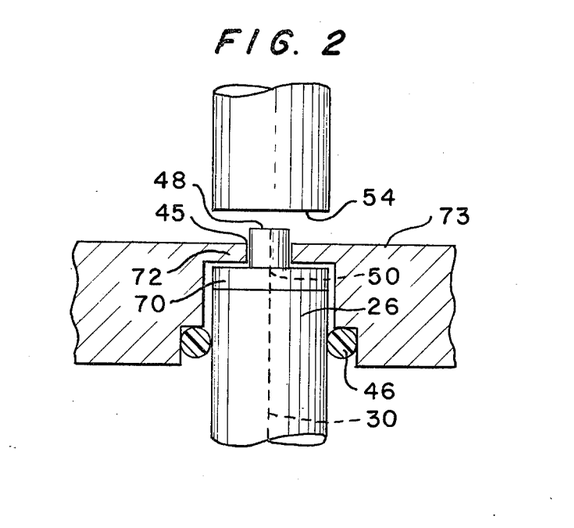
FIG. 2 is a sectional diagram showing an enlargement of a portion of the static drop mercury electrode illustrated in FIG. 1.

As embodied herein, the valve means includes means for extending a capillary passage into a mercury reservoir. As illustrated in FIGS. 1 and 2, the extension of capillary passage 30 into reservoir 12 may be accomplished by positioning first end 26 of dropping mercury capillary 24 into a capillary aperture 45 in bottom plug 34 to provide unobstructed access to reservoir 12. Preferably, first end 26 of capillary 24 is actually inserted completely through aperture 45 and is located above the lowermost portion of reservoir 12 causing first end 26 to be surrounded by mercury.

As embodied herein, the valve means further includes a first valve seat positioned in a mercury reservoir beneath the surface of the mercury. As illustrated in FIGS. 1 and 2, first end 26 of capillary 24 forms a first valve seat 48. In FIGS. 1 and 2, first end 26 of capillary 24 is shown to have a mesa or plateau section 50 which extends through capillary aperture 45, formed in bottom plug 34, and extends into reservoir 12. Capillary passage 30 extends from capillary 24 through mesa 50 and opens into reservoir 12 at a point above the lowermost portion of the reservoir, causing section 50 of first end 26 to be surrounded by mercury.

A fixed junction is formed between the outer surface of first end 26 of capillary 24 and bottom plug 34 by O-ring 46. There are no moving surfaces between capillary 24 and bottom plug 34 and thus, O-ring 46 forms a mercury and airtight seal keeping mercury 14 in reservoir 12.

As embodied herein, the valve means further includes sealing means for forming a sealing surface. As illustrated in FIGS. 1 and 2, a plunger 52 provides a sealing means having a sealing surface 54 on the lower end thereof. More specifically, sealing surface 54 comprises a portion of a disc 55 of resilient material such as polyurethane rubber attached to the end of plunger 52. In FIG. 1, plunger 52 is shown to comprise an elongated rod extending in the vertical direction upward from the general area of first valve seat 48 into reservoir 12 of housing 10. Plunger 52 is slidably mounted in housing 10 within a generally cylindrically shaped body 56 which extends from the inner surface of bottom plug 34 through reservoir 12 through an opening in cover 16 to the outside of housing 10. Body 56 is held in fixed position between bottom plug 34 and cover 16 by suitable means such as by a threadable engagement between body 56 and cover 16 and/or by threadable engagement between body 56 and bottom plug 34. Body 56 has at least one guide bushing 58 with centrally located apertures to slidably receive and locate plunger 52 within body 56. Body 56 further has a series of apertures 60 in the sidewalls thereof to allow for the free flow of mercury from reservoir 12 into the interior of body 56.

In the embodiment of the present invention illustrated in FIG. 1, the lower end of body 56 is open and positioned concentric to mesa 50 of first end 26 of dropping mercury capillary 24. Furthermore, the apertures and guide bushings 58 are positioned to allow sealing surface 54 of plunger 52 to engage first valve seat 48 at first end 26 of capillary 24.

In accordance with the present invention, the valve means of the static mercury drop electrode still further includes control means for selectively controlling the relative position of a sealing surface and a first valve seat between an open position in which the sealing surface is disengaged from the first valve seat but yet completely immersed in the mercury to allow passage of mercury from a reservoir to a capillary passage, and a closed position with the sealing surface engaged with the first valve seat to prevent passage of mercury from the reservoir into the capillary passage.

As embodied herein and illustrated in FIGS. 1 and 2, the control means is shown to include a spring biasing the sealing surface 54 of plunger 52 into the closed position and further includes a solenoid operable on plunger 52 to full sealing surface 54 into the open position against the bias of the spring. As illustrated in FIG. 1, a spring 62 is inserted between an inwardly extending collar 64 of body 56 and a pin 66 on plunger 52. The positioning of collar 64, and pin 66 is chosen to allow spring 62 to bias plunger 58 in a downward direction causing sealing surface 54 at the bottom of plunger 56 to be held fast against and in sealing relationship with first valve seat 48 to prevent passage of mercury in reservoir 12 through capillary passage 30.

In the embodiment of the present invention illustrated in FIG. 1, a solenoid 68 is shown rigidly positioned at the upper end of body 56. Solenoid 68 receives the upper end of plunger 52. The upper end of plunger 52 is preferably formed of magnetic stainless steel or other suitable material whereby upon activation of solenoid 68 by application of appropriate electrical potential thereto, solenoid 68 will operate to lift plunger 52 against the bias of spring 62 thereby disengaging sealing surface 54 from first valve seat 48.

When sealing surface 54 is first introduced to mercury, air in minute yet significant amounts can be trapped on the sealing surface as is well-known to those skilled in the art. However, after several operations of solenoid 68, all air of any significance is removed or purged from sealing surface 54 and from capillary passage 30, thereby establishing an air-purged mechanism for selectively forming hanging mercury drops.

It should be understood that solenoid 68 may be physically constructed in a manner whereby the lower casing of solenoid 68 operates in the same manner as collar 64 to support the upper end of spring 62. Furthermore, it should be understood that the control means of the present invention may employ other suitable mechanisms such as movable cam surfaces, or pneumatic or hydraulic mechanisms, in engagement with plunger 52 to selectively control the relative position of sealing surface 54 and first valve seat 48 between the open position with sealing surface 54 disengaged from first valve seat 48 to allow passage of mercury from reservoir 12 to capillary passage 30, and the closed position with sealing surface 54 engaged with valve seat 48 to prevent passage of mercury from reservoir 12 to capillary passage 30.

In accordance with the teachings of a preferred embodiment of the present invention, the static mercury drop electrode illustrated in FIG. 1 further includes means for providing electrical coupling between the mercury in the capillary passage and the mercury in the reservoir. This electrical conduction may be provided by the employment of an electrically conducting tip 70 at first end 26 of capillary 24. Metallic tip 70 may comprise, for example, plated, sputtered or evaporated metal on the first capillary end 26 which extends into the material forming the capillary to provide electrical continuity between the outer surface of the capillary which is surrounded by mercury in reservoir 12, illustrated in FIGS. 1 and 2, and the capillary passage 30. In the alternative, the first end 26 of capillary 24 may be formed of a tip 70 comprising conductive glass or plated tin oxide material or other mercury compatible conductive material. In a still further embodiment of the present invention, tip 70 may comprise a section of conducting material separate and distinct from the material forming dropping mercury capillary 24 but physically attached to first end 26 of capillary 24 in sealed engagement therewith by glue or other suitable sealing substance with the capillary passage 30 extended through the additional material, whereby the conducting material forms the conductive passage between capillary passage 30 and the mercury 14 in reservoir 12.

In accordance with the teachings of a preferred embodiment of the present invention, bottom plug 34 of housing 10 forms shoulders 72 around the mesa or plateau section 50 which extends capillary passage 30 into reservoir 12. Shoulders 72 provide a second valve seat 73 positioned below sealing surface 54 of plunger 52. Second valve seat 73 is positioned to receive sealing surface 54 when capillary 24 is removed from bottom plug 34 and sealing surface 54 is downwardly biased by spring 62. Thus, sealing surface 54 engages second valve seat 73 formed by shoulders 72, upon removal of mesa 50 from reservoir 12, to prevent passage of mercury through aperture 45 in bottom plug 34 when aperture 45 is vacated by mesa 50.

The embodiment of the present invention illustrated in FIG. 1 further includes a drop kick solenoid 74 located adjacent capillary 24 to selectively dislodge drops 32 formed at the second end 28 of the capillary.

In the operation of the static drop mercury electrode illustrated in FIGS. 1 and 2, reservoir 12 is filled with a suitable volume of mercury 14 through the opening 22 in cover 16. The mercury enters the internal portion of body 56 through apertures 60 to completely cover the upper surface of bottom plug 34 which defines reservoir 12. In the absence of a capillary, the aperture 45 in bottom plug 34 is sealed off by the engagement of sealing surface 54 of plunger 52 held fast by spring 62 against the second valve seat 73 formed by shoulders 72 at the top of plug 34.

A dropping mercury capillary 24 is inserted into bottom plug 34 and held fast by capillary nut 44. Ferrule 42 on capillary 24 abuts inwardly extending shoulders 35 of bottom plug 34 to assure that mesa section 50 of capillary 24 extends through aperture 45 into reservoir 12. As mesa section 50 engages sealing surface 54 of plunger 52, sealing surface 54 is forced out of engagement with shoulders 72 but into sealed engagement with first valve seat 48 at the end of mesa 50. Thus, no mercury is allowed to pass from reservoir 12 into capillary passage 30. Furthermore, the mercury in reservoir 12 extends completely around mesa 50, eliminating any and all air passages to capillary passage 30.

Upon selective energization of solenoid 68, plunger 52 is lifted against the bias of spring 62 to cause sealing surface 54 to disengage from first valve seat 48 and allow mercury to pass into capillary passage 30, purging or flushing out all air initially present in capillary passage 30. With solenoid 68 continuously activated and capillary passage 30 therefore continuously exposed to the mercury in reservoir 12, the electrode illustrated in FIG. 1 operates as a dropping mercury electrode or hanging drop electrode, whereby the period of drop formation at second end 28 of capillary 24 is governed by the bore size of capillary passage 30 and the height of the mercury 14 in reservoir 12.

However, in accordance with the teachings of the present invention, solenoid 68 may be activated for only a selectively short period of time, allowing only a specific volume of mercury to pass down capillary passage 30 and form a drop 32 at the second end 28 thereof. The deactivation of solenoid 68 allows spring 62 to bias sealing surface 54 once again against first valve seat 48 and therefore prevents additional flow of mercury down capillary passage 30. By activating solenoid 68 for only precisely controlled periods, mercury drops 32 are allowed to grow to a predetermined volume and surface area. At the end of the growth period, which preferably ranges from about 50 milliseconds to 250 milliseconds, the solenoid 68 is deactivated, and drop growth is arrested. The resultant mercury drop is therefore held stationary or static at the end of the capillary throughout the measuring period which follows.

Measurements may then be made by any known DC, sampled DC, integral pulse, differential pulse or other voltametric technique. Following measurement, the drop is mechanically dislodged and a new drop is generated by again activating the solenoid 68. The process then repeats. The only limitations on the ultimate speed of the static drop mercury electrode, according to the present invention, are delays presently considered necessary after generation of a drop and after dislodging of a drop to allow for vibration dampening of the electrode. The minimum complete cycle time has not yet been determined but is expected that the present invention will allow somewhere between 5 and 10 drops to be grown and dislodged per second.

To assure that the static drops 32 formed by the electrode, illustrated in FIGS. 1 and 2, are of uniform area for a given period of solenoid 68 activation, it may be necessary to regulate the pressure in reservoir 12 as the mercury level decreases. This can be accomplished by the selective introduction of a suitable gas, such as nitrogen, through large bore passage 38 to maintain a constant pressure in housing 10. In the alternative, use of a reservoir 12 of sufficient volume may result in a decrease in mercury level so slight throughout an analysis that its influence on drop size is negligible and pressurization adjustment is unnecessary. It is also possible to operate the electrode with reservoir 12 not sealed, for example, by removing screw 23.

It should be noted that, unlike the sliding gate valves of prior art large bore capillary systems, which cannot effectively prevent inclusion of air in the capillary, the present system provides an extremely secure air-tight seal between the mercury in capillary passage 30 and air. This seal results primarily from the fact that the valve seat of capillary passage 30, which is selectively opened and closed, first valve seat 48, lies completely immersed in the reservoir 12 of mercury 14. Thus, even the smallest amount of air cannot enter capillary passage 30 of the present invention. In essence, the static drop mercury electrode of the present invention provides the sealing integrity of the prior art dropping mercury electrodes which had no moving parts and relied solely on mercury column height and capillary passage diameter to establish the growth rate of hanging mercury drops, but yet, unlike the prior art electrodes, provides for periodically generating mercury drops of reproducible size at the end of a dropping mercury capillary and holding these drops static for a desired period of time, of either extremely short or long duration.

Figure 3:
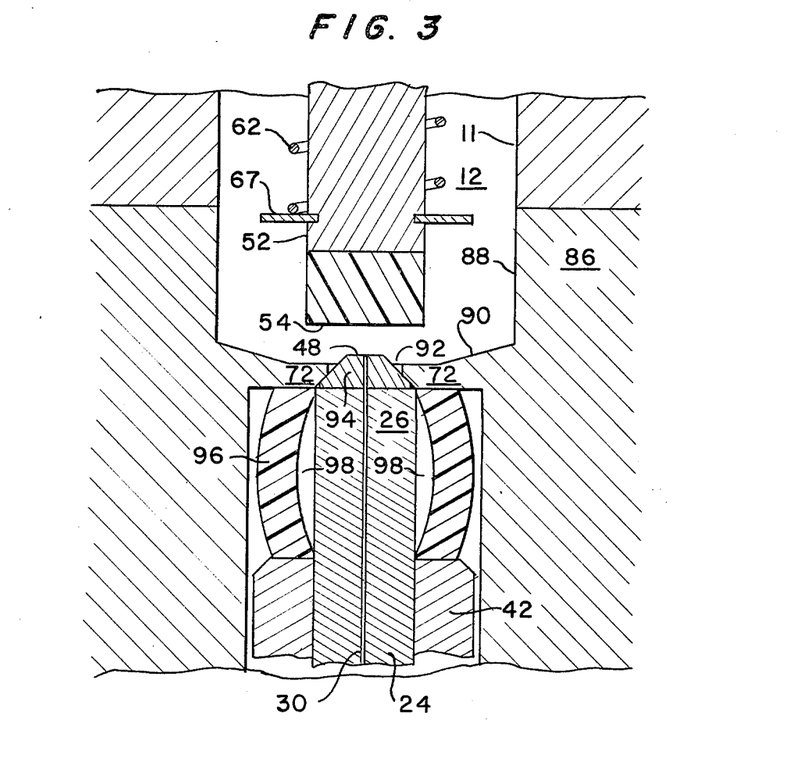
FIG. 3 is another embodiment of a portion of the static drop mercury electrode in accordance with the teachings of the present invention.

FIG. 3 illustrates an alternative preferred embodiment of the present invention.

In FIG. 3, sidewalls 11 of the housing 10 are shown to be mounted in fixed relation with a bottom plug 86, which functions in essentially the same manner as bottom plug 34 of FIGS. 1 and 2. However, bottom plug 86 is illustrated as having an indentation defined by sidewalls 88 and bottom wall 90. Bottom wall 90 has an aperture 92 in shoulders 72 located immediately below sealing surface 54 of plunger 52. As illustrated in FIG. 1, plunger 52 has a retaining ring 67 in engagement with spring 62 and spring 62 operates against ring 67 and another surface of housing 10, not illustrated in FIG. 3, to bias sealing surface 54 against bottom wall 90 to close off aperture 92.

Accordingly, bottom wall 90 of the embodiment of the present invention illustrated in FIG. 3, operates in substantially the same manner as shoulders 72 of the embodiment shown in FIGS. 1 and 2 to form a second valve seat.

In FIG. 3 the first end 26 of the dropping mercury capillary is shown to include a beveled or radiused electrically conducting tip 94 which functions similarly to tip 70 illustrated in FIGS. 1 and 2. As was true with tip 70, tip 94 may be formed of plated, sputtered or evaporated metal, of conductive glass or of coated conductive materials such as tin oxide. Furthermore, tip 94 may be formed of a separate piece of conducting material physically attached to capillary 24.

As was true with the mesa section 50 of tip 70, a portion of tip 94 extends through aperture 92 into reservoir 12. Thus, the upper surface of first end 26 again forms a first valve seat 48 capable of sealing engagement with sealing surface 54 of plunger 52.

The embodiment of the present invention illustrated in FIG. 3 further shows a piece of resilient tubing sleeve 96 surrounding first end 26 of capillary 24 and located between ferrule 42 and the lower surface of shoulders 72. Upon tightening of a capillary nut below ferrule 42 to force ferrule 42 in an upward direction, sleeve 96 bows outward in response to the compression of sleeve 96 between ferrule 42 and shoulders 72. Thus, pockets 98 between tubing 96 and capillary 24 expand as ferrule 42 is forced toward shoulders 72. The expansion of the volume of pockets 98 causes a pressure differential which tends to pull mercury from reservoir 12, past shoulder 72 and tip 94, into pockets 98 and prevent the flow of any air between shoulders 72 and tip 94 into reservoir 12. Accordingly, sleeve 96 provides for the integrity of the seal between capillary passage 30 and reservoir 12, to the exclusion of any air.

Figure 4:
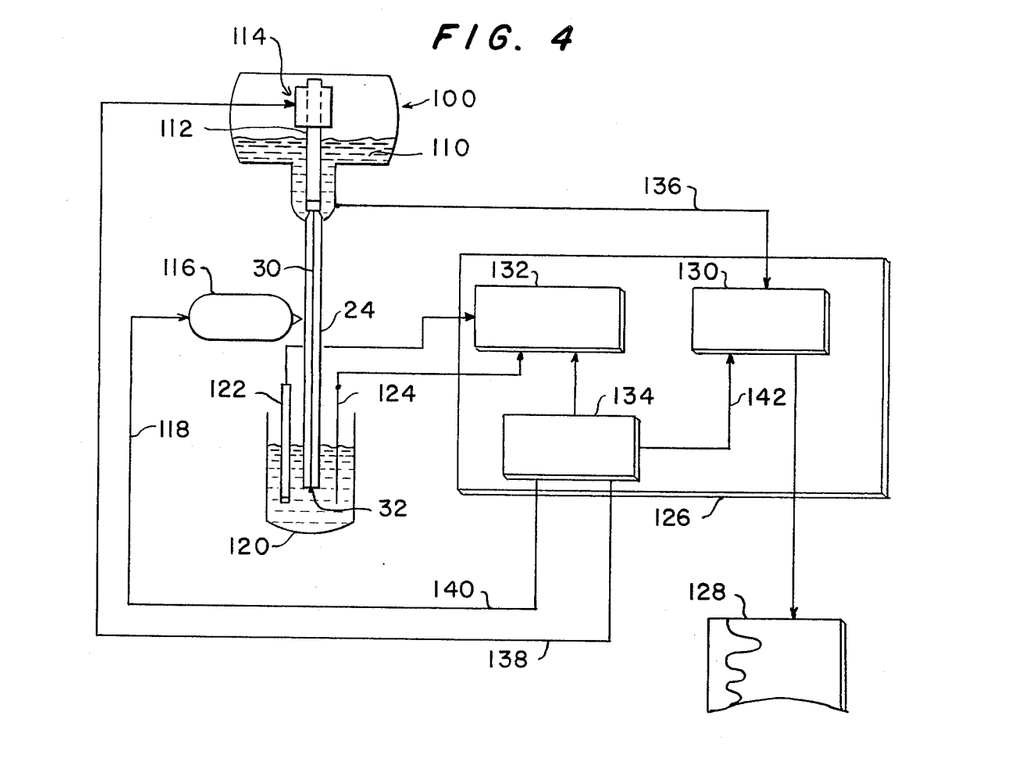
FIG. 4 is a block diagram of a system employing the static drop mercury electrode of the present invention.

FIG. 4 illustrates a system employing the static drop mercury electrode of the present invention.

A static drop mercury electrode 100 is illustrated generally by a housing 110, a plunger 112, and a solenoid 114 which controls plunger 112 as set out above with respect to FIGS. 1 through 3. Furthermore, a capillary 24 is shown extending downward from housing 100 and having a capillary passage 30 therein. It is to be understood that static drop mercury electrode 100 operates as described above with respect to FIGS. 1 through 3, whereby activation of solenoid 114 results in the growth of a mercury drop 32 at the lower end of capillary 24, which drop 32 is held stationary upon deactivation of solenoid 114 and return of plunger 112 into a position which seals off capillary passage 30 from the reservoir in housing 110.

The apparatus illustrated in FIG. 4 further shows a drop kick solenoid 116 positioned adjacent capillary 24, which, upon selective activation by a control signal over control line 118, imparts a mechanical shock to capillary 24, sufficient to dislodge drop 32 from the end of capillary passage 30.

FIG. 4 further illustrates an electrolysis cell 120 containing a solution under analysis. In FIG. 4, static drop mercury electrode 100 is illustrated as being immersed in the solution to be tested and providing a working or indicating electrode of electrolysis cell 120. Electrolysis cell 120 further employs a reference electrode 122 and an auxiliary or counter-electrode 124 immersed in the solution.

In FIG. 4, static drop mercury electrode 100 is being operated to provide polarographic analysis. More specifically, a polarographic analyzer 126 is connected to static drop mercury electrode 100 to provide an output at recorder 128. Polarographic analyzer 126 may, for example, comprise the publically available Princeton Applied Research Corporation Polarographic Analyzer Model 174. Model 174 contains a current-to-voltage converter 130, a potentiostat 132 and a timing and control logic unit 134.

As is well known to those skilled in the art, and in particular as is well known to those who utilize the Model 174 polarographic analyzer, an electrical conductor 136 which electrically connects the mercury in the mercury drop electrode to the current-to-voltage converter 130 of polarographic analyzer 126. In FIG. 4, current-to-voltage converter 130 not only converts the current from static drop mercury electrode 100 to voltage but also effectively maintains static drop mercury electrode 100 at essentially ground potential.

As is also fully understood to those skilled in the art, potentiostat 132 is connected to a reference electrode 122 and to counter electrode 124 in a manner whereby counter electrode 124 is utilized to establish a desired electrical potential between reference electrode 122 and mercury drop 32 of static drop mercury electrode 100.

Timing and control logic unit 134 has a first output coupled by line 138 to solenoid 114 of stationary drop mercury electrode 100 and a second output coupled by line 140 to drop kick solenoid 116. The output of timing and logic control unit 134 and the interconnection between timing and control logic unit 134 to potentiostat 132 and to current-to-voltage converter 130 can be more readily explained with reference to FIG. 5.

Figure 5:
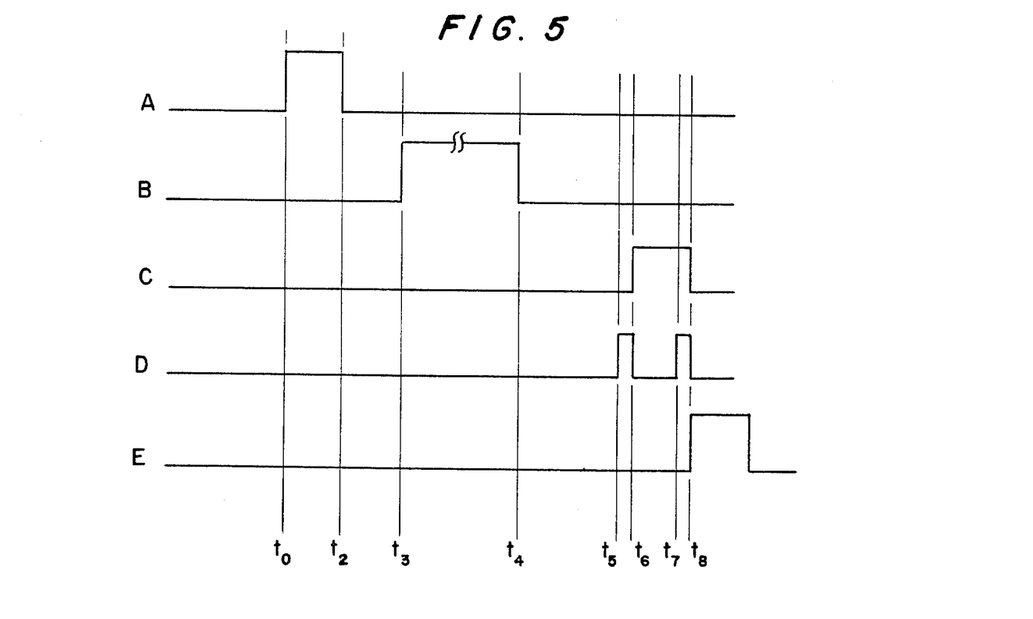
FIG. 5 is a series of timing charts illustrating the system illustrated in FIG. 4.

FIG. 5 provides timing graphs of the operation of the apparatus illustrated in FIG. 4.

More specifically, graph A of FIG. 5 illustrates that timing and control logic unit 134 generates a control signal to drop kick solenoid 116 at a time $T_0$ having a duration of between 20 to 30 milliseconds. The energization of drop kick solenoid 116 causes drop kick solenoid 116 to impart a mechanical thump to capillary 24 which dislodges any drop formed at the lower end of capillary 24. It is presently believed by the inventors that mechanical movement imparted to capillary 24 by drop kick solenoid 116 sufficient to dislodge a drop 32 sets up vibrations within the system which are sufficiently damped after a delay of approximately 50 milliseconds between the termination of the drop kick pulse in graph A at time $T_2$ and the beginning of a dispense pulse at time $T_3$ appearing on control line 138.

The dispense pulse from timing and control logic unit 134, shown in graph B of FIG. 5, energizes solenoid 114 for a specifically controlled duration of time to allow mercury to pass from the reservoir in housing 110 down capillary 30 to form a drop of predetermined surface area at the tip of capillary 24. For example, with 2 psi pressure above the capillary 24, a duration of dispense pulse from $T_3$ to $T_4$ encompassing 50 milliseconds produces what is considered a small drop at the lower end of capillary 24 when capillary passage 30 has a bore diameter of approximately 6/1000 inch. A time period between $T_3$ and $T_4$ of approximately 100 milliseconds produces what is considered a medium drop size and a time period duration of 200 milliseconds produces what is considered a large drop size. Varying the duration of the period from $T_3$ to $T_4$ can readily be accomplished by those skilled in the art by controlling the dispense pulse on line 40 from timing and control logic unit 134.

Upon termination of the dispense pulse at time $T_4$ solenoid 114 is deactivated and plunger 112 is moved into a position whereby mercury is once again precluded from entering the capillary passage 30 of capillary 24. Thus, for the time period following $T_4$, the drop 32 at the end of capillary 24 is held stationary.

Once a stationary drop is produced at the end of capillary 24, any known voltametric measuring technique which requires a stationary drop may be performed, using static drop electrode 100. In the apparatus illustrated in FIGS. 4 and 5, the voltametric technique employed is illustratively chosen to be of the differential pulse polarographic type well-known to those skilled in the art.

In accordance with known differential pulse polarographic techniques, a first sample of working electrode current is taken before application of a modulation, shown in graph B of FIG. 5, and a second sample of working electrode current is taken just before termination of the modulation pulse. The difference between the two pulse samples provides an analytical signal of interest in analyzing the solution under analysis. As is known to those skilled in the art, the current-to-voltage converter 130 of Model 174 polarographic analyzer compares working electrode current during the two sampling pulses and produces for each reducible material in solution a distinct and separate output signal peak on recorder 128.

While it is outside the scope of the present invention to provide a detailed analysis of the internal connections of polarographic analyzer 126, it should be understood that the timing and control logic unit 134 communicates the first sampling pulse, illustrated in graph D of FIG. 5, over line 142 in FIG. 4 to current-to-voltage converter 130. Typically, the first sampling period is of a 17 millisecond duration. Immediately following the termination of the first sampling period, timing and control logic unit 134 generates a modulation pulse over line 144 to potentiostat 132, as illustrated in graph C of FIG. 5, to cause potentiostat 132 to apply suitable potential to reference electrode 122. The modulation pulse typically has a duration of approximately 50 milliseconds. Just prior to the termination of the modulation pulse, a second sampling pulse is generated by timing and voltage control logic unit 134 over line 142 to current-to-voltage converter to once again activate current to voltage converter for approximately a 17 millisecond duration.

Upon the simultaneous termination of the modulation pulse, illustrated in graph C, and the second sampling pulse, illustrated in graph D of FIG. 5, the cycle begins again with the generation by timing and control logic unit 134 of a drop kick pulse illustrated in graph E of FIG. E.

It is understood that the larger the drop 32 formed at the end of capillary 24, the more sensitive the polarographic analyzer 126 is to the content of solution under analysis. However, it has been found that the larger the drop, the longer the required delay period between the termination of the dispense pulse, illustrated in graph B, and the initiation of the first sample pulse of graph D. Specifially, the minimum period between $T_4$ and $T_5$ is that time required to allow the solution under analysis in cell 120 to become quiescent after formation of drop 32. Typically, a minimum period of 180 milliseconds is required. However, suitable analysis can be obtained using quiescent periods between $T_4$ and $T_5$ throughout the range of 180 milliseconds to 4–178 seconds.

The advantages of employing the static drop mercury electrode 100 of the present invention are many. For example, by assuring the same area of mercury drops during the first pulse sample in graph D and the second pulse sample 3 in graph D, the sensitivity of the system is greatly increased, since the background noise during both samples is the same and can be substantially cancelled out. To the contrary, in prior art differential pulse polarographic systems, the drop continues to grow between the first and second sampling pulses. Furthermore, because the area of the drop is held constant during both sampling pulses, the drop 32 can be formed to an optimum size since no further growth will be encountered which would risk premature dislodging of drop 32 from capillary 24.

The static drop mercury electrode of the present invention further provides a substantial advancement over the prior art techniques of establishing stationary mercury drops for long periods of time by allowing for early and constant formation of uniform drops. The present invention also represents a substantial advancement over U-shaped large bore sessile drop electrodes since the present invention provides the advantages of a static drop which is not supported by the capillary but rather hangs freely suspended from the capillary in the solution and therefore is of more perfect spherical shape than a sessile drop. Finally, as outlined above, the present stationary drop mercury electrode is designed with a valve arrangement secure against air leaks into the mercury column and is therefore free from any pockets of air in capillary 30 and is therefore free from the detrimental effects of such pockets of trapped air experienced in the prior art.

While a particular embodiment of the present invention has been shown and described, it will, of course, be obvious to one skilled in the art that certain advantages and modifications may be effected without departing from the spirit of the invention, and accordingly, it is intended that the scope of the invention not be determined by the foregoing examples but only by the scope of the appended claims.

What is claimed is:

1. A static mercury drop electrode comprising:
   a housing forming a reservoir for liquid mercury;
   a dropping mercury capillary having first and second ends and forming a capillary passage therebetween with said capillary passage terminating in a downward direction at said second end; and
   valve means for selective air-purging passage of mercury from said reservoir to said first end of said capillary to form static mercury drops at said second end of said capillary, said valve means including a valve seat positioned in said reservoir beneath the surface of said mercury at said first end of said capillary, sealing means for forming a sealing surface, and control means for selectively controlling the relative position of said sealing surface and said valve seat between an open position with said sealing surface disengaged from said first valve seat and in contact with mercury in said reservoir, and a closed position with said sealing surface engaged with said first valve seat to prevent flow of said mercury from said reservoir to said capillary passage.

2. The static mercury drop electrode according to claim 1 wherein said first end of said capillary forms said first valve seat.

3. The static mercury drop electrode according to claim 2 wherein said first end of said capillary is located above the lowermost portion of said reservoir, causing said first end to be surrounded by mercury.

4. The static mercury drop electrode according to claim 1 including means for providing electrical coupling between mercury in said capillary passage and mercury in said reservoir.

5. The static mercury drop electrode according to claim 1 wherein said sealing means comprises a plunger with said sealing surface formed on one end thereof, said plunger being mounted in said housing for movement by said control means co-linear with the axis of said capillary.

6. The static mercury drop electrode according to claim 5 wherein said control means includes a spring biasing said sealing surface of said plunger into said one of said positions and further includes a solenoid operable on said plunger to bias said sealing surface into the other of said positions.

7. The static mercury drop electrode according to claim 6 wherein said housing forms a sealed reservoir and said housing further includes means for providing access to said reservoir to allow maintenance of a constant pressure on said mercury at said first end of said capillary.

8. The static mercury drop electrode according to claim 1 wherein said housing forms a second valve seat adjacent said capillary and said sealing surface is adapted to engage said second valve seat upon removal of said capillary passage extending means from said reservoir.

9. A static mercury drop electrode comprising:
   a housing forming a reservoir for mercury;
   a dropping mercury capillary extending from said housing, said capillary having first and second ends and forming a capillary passage from said reservoir at said first end to said second end with said capillary passage terminating in a downward direction at said second end and said passage being of sufficiently small diameter to form hanging mercury drops at said second end, an air-impervious valve means for forming a selectively operable air-purging passage from said reservoir to said first end of said capillary to allow controlled formation of static mercury drops at said second end of said capillary, said valve means including a first valve seat formed by said first end of said capillary and positioned in said reservoir beneath the surface of said murcury, sealing means for forming a sealing surface, and control means for selectively moving said sealing surface between an open position with said sealing surface disengaged from said first valve seat and in contact with said mercury in said reservoir and a closed position with said sealing surface engaged with said first valve seat to prevent passage of said mercury in said reservoir to said capillary.

10. The static mercury drop electrode according to claim 9 wherein said first end of said capillary is located above the lowermost portion of said reservoir causing said first end to be surrounded by mercury in said open condition.

11. The static mercury drop electrode according to claim 9 including means for electrically connecting mercury in said capillary passage with mercury in said reservoir.

12. The static mercury drop electrode according to claim 11 wherein said sealing means comprises a plunger with said sealing surface formed on one portion thereof, said plunger being mounted in said housing for movement by said control means co-linear with the axis of said capillary.

13. The static mercury drop electrode according to claim 12 wherein said control means includes a spring to bias said sealing surface of said plunger into said closed position and further includes a solenoid operable on said plunger to pull said sealing surface into said open position.

14. The static mercury drop electrode according to claim 13 wherein said housing has an aperture to receive said capillary and said housing has a second valve seat positioned to engage said sealing surface upon removal of said extending means from said reservoir and to prevent passage of mercury through said aperture.

15. A static mercury drop electrode comprising:
a housing for holding liquid mercury;
a hanging drop capillary extending vertically downward from said housing with the upper end of said capillary extending into said housing to form a first flat surface and said capillary being of sufficiently fine bore to allow formation of hanging mercury drops at the lower end of said capillary; and
a plunger moveably mounted in said housing and having a lower second flat surface immersed in said mercury paralled to said first flat surface, said second flat surface of said plunger selectively moveable in a direction to intersect the plane defined by said first flat surface and engageable with said first flat surface to allow selective formation of static mercury drops at the lower end of said capillary.

16. The static mercury drop electrode according to claim 15 wherein said upper end of said capillary is located above the lowermost portion of said reservoir causing said first end to be completely surrounded by mercury when said lower surface of said plunger is disengaged therefrom.

17. The static mercury drop electrode according to claim 16 including means for electrically connecting mercury in said capillary with mercury in said housing.

18. The static mercury drop electrode according to claim 17 including a spring to bias said lower surface of said plunger against the upper surface of said capillary, and further comprising a solenoid operable on said plunger to pull said lower surface of said plunger away from said upper end of said capillary.

19. The static mercury drop electrode according to claim 18 wherein said housing has an opening to receive said capillary and said housing has a surface surrounding said opening and said plunger is biased by said spring to engage said surface and close said opening upon removal of said capillary from said reservoir.

20. The static mercury drop electrode according to claims 1 or 9 wherein said sealing means comprises a plunger with said sealing surface formed on one end thereof, said plunger being mounted in said housing for movement of said sealing surface by said control means in a direction which intersects a plane defined by the surface of said valve seat.

* * * * *

Dedication 4,260,467.—*John L. Smith,* Mercerville, and *Bruce N. Whitlock,* Princeton, N.J. STATIC DROP MERCURY ELECTRODE. Patent dated Apr. 7, 1981. Dedication filed Apr. 22, 1982, by the assignee, *Princeton Applied Research Corp.*

Hereby dedicates to the Public the entire term of said patent.
[*Official Gazette August 24, 1982.*]

UNITED STATES PATENT AND TRADEMARK OFFICE
CERTIFICATE OF CORRECTION

PATENT NO. : 4,260,467

DATED : April 7, 1981

INVENTOR(S) : John L. Smith and Bruce N. Whitlock

It is certified that error appears in the above-identified patent and that said Letters Patent is hereby corrected as shown below:

Column 16, line 2, Claim 14, "said extending means" should read -- said capillary --.

Signed and Sealed this

Twenty-second Day of November 1983

[SEAL]

Attest:

GERALD J. MOSSINGHOFF

Attesting Officer   Commissioner of Patents and Trademarks